United States Patent [19]

Sablon

[11] Patent Number: 5,559,146
[45] Date of Patent: Sep. 24, 1996

[54] **METHOD OF USING COSMETIC COMPOSITIONS COMPRISING AN EXTRACT OF *ECLIPTA ALBA***

[76] Inventor: Lewis E. Sablon, Rue Lethière, 97180 Sainte-Anne, Guadeloupe, France

[21] Appl. No.: 182,026

[22] PCT Filed: Jul. 17, 1992

[86] PCT No.: PCT/FR92/00699

§ 371 Date: Jul. 27, 1994

§ 102(e) Date: Jul. 27, 1994

[87] PCT Pub. No.: WO93/01796

PCT Pub. Date: Feb. 4, 1993

[30] Foreign Application Priority Data

Jul. 19, 1991 [FR] France ................... 91 09184

[51] Int. Cl.$^6$ ............... A61K 31/34; A61K 35/78
[52] U.S. Cl. ............... 514/468; 424/195.1; 424/62
[58] Field of Search ............... 424/195.1, 62; 514/468

[56] References Cited

FOREIGN PATENT DOCUMENTS 3525363  10/1987  Germany.

OTHER PUBLICATIONS

Chem. Abst. 106:27529y, 1987.
Chem. Abst. 106:125872z, 1987.
Chem. Abst. 78:97958q, 1973.
Chem. Abst. 74:9684m, 1971.
Chem. Abst. 74:1021x, 1971.
STN Database Server, Karlsrue, Germany, Fichier Chemical Abstracts, vol. 113, No. 12, (Columbus, OH, U.S.) see abstract No. 103209f and CN,A, 1031022 (Tianjin Institute of Light Industrial Chemistry) Feb. 15, 1989, see abstract.

*Primary Examiner*—John W. Rollins
*Attorney, Agent, or Firm*—Browdy and Neimark

[57] ABSTRACT

Cosmetic composition for the regulation of skin pigmentation, comprising wedelolactone an/or desmethylwedelactone or an extract of *Eclipta alba*.

11 Claims, No Drawings

METHOD OF USING COSMETIC COMPOSITIONS COMPRISING AN EXTRACT OF *ECLIPTA ALBA*

FIELD OF THE INVENTION

The invention relates to new cosmetic compositions which allow the regulation of cutaneous pigmentation.

BACKGROUND OF THE INVENTION

Irregularities in the pigmentation of the skin have always been considered unsightly, and for some considerable time various means have been proposed to remedy this.

These defects appear most often in the form of hyperpigmentation blemishes, which may take diverse forms: freckles, chloasma of hormonal origin, senile lentigo located mainly on the hands, hyperpigmentation related to scars or resulting from a photosensitizing agent, and the like.

A most diverse range of approaches has been proposed for removing these blemishes, and whitening the skin, imparting a uniform coloration thereto. The use of numerous substances of animal or mineral origin, as well as of a large variety of plants and substances of vegetable origin, has been recommended for this purpose. The publication of SCARPA and GUERCI [Journal of Ethnopharmacology, 19 17–66 (1987)] reveals the diversity of the preparations proposed.

However, a very small number of the formulations thus proposed have shown any real proof of their effectiveness. At the present time, very few substances are known which have a real depigmenting effect, and among these substances the majority exhibit annoying, or even harmful, side effects.

For example, certain preparations based on mercury salts, although endowed with a real power for lightening the skin, present real danger, because the transcutaneously absorbed mercury may cause serious poisoning.

The majority of the depigmenting preparations currently available commercially contain hydroquinone as the active ingredient. These preparations are, however, not without disadvantages. They are in fact very difficult to handle: their application must effectively be strictly limited to the regions to be depigmented, and the amount used must be carefully dosed. These disadvantages are particularly important for subjects of dark skin, for whom there is a risk of new blemishes appearing resulting from a non-uniform depigmentation. In addition, hydroquinone is poorly tolerated by many people, in whom it provokes skin irritations.

Among the innumerable active principles of vegetable origin, or extracted from plants, to which a depigmenting action has been attributed, only one is effectively used in cosmetology: this is an extract of the common yarrow, whose activity is thought to arise from the presence of luteolin and its heterosides.

The Inventor has undertaken research with the aim of discovering other substances which regulate pigmentation without, however, exhibiting the disadvantages of the substances currently used.

It is in fact desirable to have available substances which remove pigmentation blemishes without, however, provoking a general whitening of the skin or else an excessive depigmentation of the regions treated. It is in addition necessary for these active principles to be well tolerated and, in particular, not to provoke irritation.

SUMMARY OF THE INVENTION

Now, the Inventor found that extracts obtained from the plant *Eclipta alba* possessed depigmenting properties, without provoking the side effects mentioned above. By fractionating the extracts obtained, the Inventor additionally found that these properties were associated with the fraction of the plant which is rich in flavonoids, and that preparations containing wedelolactone or demethylwedelolactone, which are the main flavonoids of *Eclipta alba*, also possessed depigmenting properties.

*Eclipta alba* is a plant which belongs to the family Compositae, and which is frequently encountered in tropical regions (India, Africa, West Indies, Guyana). This plant has been the subject of diverse studies which have resulted in the discovery of various active principles. Thus BHARGAVA et al. [Indian Journal of Chemistry, 10 810–811 (1972)] extracted 3 isoflavonoids from the leaves: wedelolactone, demethylwedelolactone and its glucoside. QUISUMBING [Medicinal Plants of the Philippines: Technical Bulletin—Department of Agriculture and Natural Resources—Republic of the Philippines, Manila; 16, 1234 (1951)] discovered resins, as well as an alkaloid: ecliptine. KARRER [Konstitution und Vorkommen der Organischen Pflanzenstoffe, Birkhäuser Verlag—Basle and Stuttgart, 1st Vol. p. 1207, (1958); Supplement I p. 1038, (1977); Supplement II p. 939, (1981)] described the presence of a sterol: stigmasterol. HEYWOOD et al. [The Biology and Chemistry of the Compositae—Academic Press, London (1977)] mentioned that the aerial parts contained nicotine.

Conventional medicine has proposed various uses for *Eclipta alba;* in particular, in the West Indies, the crushed roots have been used as an anti-haemorrhagic agent, as well as in the treatment of leprosy. Some studies have led to an anti-viral activity being attributed to this plant [DHAR et al., Indian J. Exp. Biology, 232–247 (1968)], and more recently, some in vitro anti-bacterial activity [PHADKE S. A., Indian J. Med. Sci. 43:(5), 113–117, (1989)]. A review of the various known uses has been published by H. M. BURKILL ["The Useful Plants of West Tropical Africa", Vol. 1, 466–468, Royal Botanic Gardens, Kew, (1985)].

However, hitherto, no activity of *Eclipta alba* on skin pigmentation defects has been shown.

The present invention relates to cosmetic compositions for the regulation of cutaneous pigmentation, characterized in that they comprise, as active principle, wedelolactone and/or demethylwedelolactone.

According to a preferred embodiment of the cosmetic compositions according to the invention, they comprise between 0.1 and 15% by weight of wedelolactone and/or between 0.1 and 15% by weight of demethylwedelolactone.

Compositions containing low doses (less than 0.5% of each of the active principles) will preferably be used preventively, or in a maintenance treatment. Compositions containing higher doses (between 0.5 and 2%) will preferably be used for the treatment of pigmentation defects which are already established. The compositions containing the highest doses (more than 2%) will be preferred for vigorous treatments, in particular in the case of long-established pigmentation irregularities. In some special cases, compositions containing even higher doses may be readily used, by virtue of the excellent tolerability of these active principles. Thus, the Inventor has successfully tested a concentrated aqueous alcoholic extract of *Eclipta alba* comprising 10% of demethylwedelolactone and 7% of wedelolactone, without observing any side effects other than a slight drying of the skin, attributable to the alcohol content of the extract.

According to a preferred embodiment of the cosmetic compositions according to the invention, the said active principle is present in the form of an extract of plants which are rich in wedelolactone and/or in demethylwedelolactone.

The presence of wedelolactone and demethylwedelolactone in large quantities has been described for various plants, belonging particularly to the family Composite, for example *Wedelia*; extracts of these plants can consequently be employed to obtain compositions in accordance with the invention; however, in the course of experiments carried out by the Inventor, the best results were obtained using an extract of *Eclipta alba*.

According to a preferred arrangement of this embodiment, the said vegetable extract is an extract of *Eclipta alba*; advantageously, it is an extract enriched in flavonoids.

An extract enriched in flavonoids is, for example, an aqueous-alcoholic extract obtained from leaves of *Eclipta alba*, which may be concentrated, so as to contain preferably between 5 and 25% by weight of demethylwedelolactone and between 2 and 15% by weight of wedelolactone.

Advantageously, the cosmetic compositions according to the invention comprise between 1 and 25% by weight of aqueous alcoholic extract of leaves of *Eclipta alba*.

The extract of *Eclipta alba* can be combined with various excipients, as well as with other active principles known per se, to obtain preparations which are suited to different skin types and which are able where appropriate to combine the depigmenting action with another treating action (moisturizing agents, anti-wrinkle agents, emollients, anti-seborrhoeic agents, and the like).

The cosmetic preparations according to the invention are particularly effective on brown or black melanin-based hyperpigmentations related to scars or resulting from a photosensitizing agent, as well as on the hyperpigmentations of senile lentigo.

Advantageously, to obtain cosmetic preparations more particularly intended for the treatment of freckles one hormonal hyperpigmentations (chloasma), an extract of *Betula alba* is combined with the compositions according to the invention.

The silver birch (*Betula alba*) is among the plants which are traditionally recommended for lightening the skin, although no real study of its effectiveness has been carried out. Now, the Inventor found that the activity of the compositions according to the invention on hyperpigmentations of the freckle or chloasma type was considerably enhanced when a preparation based on silver birch sap was combined therewith.

The excipients used in the production of the preparations according to the invention may be very varied, and will be chosen in accordance with the type of preparation which it is desired to obtain: milk, lotion, cream, gel, ointment, suncream, make-up foundation, body milk, and the like.

Regular use of the preparations for the regulation of cutaneous pigmentation according to the invention makes it possible to remove gradually pigmentation defects and to obtain a uniform skin colouring, and exhibits none of the disadvantages of the preparations of the prior art, in particular those based on hydroquinone. On the contrary, the preparations according to the invention are perfectly tolerated, and can be used over long periods, or even preventively, without any particular precaution for their use being necessary.

DETAILED DESCRIPTION OF THE INVENTION

The present invention will be better understood with the aid of the additional description which follows, which makes reference to examples of the preparation and use of the depigmenting compounds according to the invention.

It goes without saying, however, that these examples are given solely by way of illustration of the subject of the invention, of which they in no way constitute a limitation.

EXAMPLE 1

Production of an Aqueous-Alcoholic Extract from Leaves of *Eclipta alba*

250 g of *Eclipta alba* leaves are extracted, by maceration over 48 hours, in 1000 g of 70° strength ethanol in the presence of 2% of acetic acid. After filtration, the solution is concentrated by evaporation to ⅓ of its initial volume.

This concentrated solution contains, per 100 g, 9 g of demethylwedelolactone and 6 g of wedelolactone.

EXAMPLE 2

Production of an Extract of *Betula alba*

20 g of silver birch sap are dissolved in 100 g of alcohol at 30° C.

EXAMPLE 3

Preparation of Cosmetic Compositions According to the Invention

| A) LIQUID CREAM | |
|---|---|
| Liquid paraffin | 8 g |
| Perhydrosqualene | 5 g |
| Tefose 2561 (GATTEFOSSE) | 10 g |
| Arlamol HD (ICI) | 6 g |
| Arlamol D4 (ICI) | 2 g |
| Carbopol 940 (POLYPLASTIC) | 0.3 g |
| *Eclipta alba* (concentrated extract) | 5 g |
| Methyl para-hydroxybenzoate | 0.02 g |
| Propyl para-hydroxybenzoate | 0.01 g |
| Triethanolamine | 0.3 g |
| Ensolex filter 8021 (MERCK) | 2 g |
| Water | QS 100 g |
| B) THICK CREAM | |
| Liquid paraffin | 8 g |
| Perhydrosqualene | 5 g |
| Tefose 2561 (GATTEFOSSE) | 10 g |
| Arlamol HD (ICI) | 6 g |
| Arlamol D4 (ICI) | 2 g |
| Carbopol 940 (POLYPLASTIC) | 0.3 g |
| *Eclipta alba* (concentrated extract) | 15 g |
| *Betula alba* (extract) | 5 g |
| Triethanolamine | 0.3 g |
| Methyl para-hydroxybenzoate | 0.02 g |
| Propyl para-hydroxybenzoate | 0.01 g |
| Water | QS 100 g |

C) PREPARATION PROCESS

I) Disperse the Carbopol in ⅔ of the total quantity of water. Allow to swell;

II) Weigh and place the liquid paraffin, perhydrosqualene, Tefose and Arlamol HD on a water bath to dissolve;

III) Weigh the active ingredients (extract of *Eclipta alba* and/or extract of *Betula alba*), dissolve therein the methyl and propyl para-hydroxybenzoates;

IV) Weigh the triethanolamine and dissolve it in the remaining ⅓ of water;

V) Weigh the Arlamol D4;

After bringing the mixtures I) and II) to 90° C., mix with a turbo-mixer.

At 40° C. add the mixture III), then the Arlamol D4, and then neutralize by adding the mixture IV).

| D) GEL | |
|---|---|
| Carbopol 940 | 0.5% |
| Triethanolamine | 0.5% |
| *Eclipta alba* (concentrated extract) | 10% |
| Water | QS 100 |

EXAMPLE 4

Use of the Cosmetic Compositions according to the Invention

An experiment was carried out on 3 subjects having a chloasma, 2 subjects having freckles, 4 subjects having hyperpigmentation related to acne scars and 3 subjects having a senile lentigo. The formulation described in Example 3-B, with the exception of the extract of *Betula alba,* was applied twice daily to the regions to be treated, for 2 months.

No particular sun protection was used during the treatment.

The results are as follows:

In the subjects having an hyperpigmentation related to scars, as well as in those having a senile lentigo, an attenuation of the blemishes and a unification of the skin colour is observed from the third week. At the end of two months of treatment, the hyperpigmentation related to scars has virtually disappeared in 3 of the 4 subjects, and is very strongly attenuated in the fourth. The lentigo blemishes are very attenuated and the skin coloration is uniform in the 3 subjects treated.

In the subjects having freckles and those having a chloasma, a slight attenuation is observed at the end of the two months of treatment. The treatment is continued for 2 months by the subjects, using the complete formulation of Example 3-B (that is to say, comprising the extract of *Betula alba*).

At the end of these 2 additional months of treatment, a very clear attenuation of the chloasma is observed in the 3 subjects treated, and even an almost total disappearance in one of them, and a significant attenuation of the freckles (visible uniformity of the complexion) in the 2 subjects concerned.

I claim:

1. A method for regulating cutaneous pigmentation comprising applying to the skin of a patient in need thereof a composition comprising as an active ingredient an effective amount to regulate pigment of a compound selected from the group consisting of wedelolactone, demethylwedelolactone, and mixtures thereof.

2. The method according to claim 1 wherein said active ingredient is selected from the group consisting of between 0.1 and 15% by weight of wedelolactone, between 0.1 and 15% by weight of demethylwedelolactone, and 0.1 and 15% by weight of wedelolactone and between 0.1 and 15% by weight of demethylwedelolactone.

3. The method according to claim 1 wherein said active ingredient is present in the form of an aqueous alcoholic plant extract which is rich in wedelolactone, demethylwedelolactone, or mixtures thereof.

4. The method according to claim 3 wherein said active ingredient is present in the form of an aqueous alcoholic extract obtained from leaves of *Eclipta alba.*

5. The method according to claim 4 wherein said compositions comprise from 1 to 25% of an aqueous alcoholic extract of leaves of *Eclipta alba.*

6. The method according to claim 1 wherein said composition further includes an aqueous alcoholic extract of *Betula alba.*

7. The method according to claim 6 wherein said active ingredient is present in the form of an aqueous alcoholic plant extract which is rich in wedelolactone, demethylwedelolactone, or mixtures thereof.

8. The method according to claim 7 wherein said active ingredient is present in the form of an of an aqueous alcoholic extract obtained from leaves of *Eclipta alba.*

9. The method according to claim 8 wherein said compositions comprise from 1 to 25% of an aqueous alcoholic extract of leaves of *Eclipta alba.*

10. The method according to claim 1 wherein said composition contains a cosmetically acceptable excipient.

11. The method according to claim 10 wherein said cosmetically acceptable excipient is selected from the group consisting of milks, lotions, creams, gels, ointments, suncreens, makeup foundations, and body milks.

* * * * *